United States Patent [19]

Baensch et al.

[11] Patent Number: 5,776,526
[45] Date of Patent: Jul. 7, 1998

[54] LOW-TEMPERATURE INACTIVE INDUSTRIAL BAKER'S YEAST AND PROCESS FOR PREPARING SAME

[75] Inventors: Johannes Baensch, Landridge Cond., Singapore; Christof Gysler, Blonay; Peter Niederberger, Epalinges, both of Switzerland

[73] Assignee: Nestec S.A., Vevey, Switzerland

[21] Appl. No.: 404,679

[22] Filed: Mar. 15, 1995

[30] Foreign Application Priority Data

Mar. 16, 1994 [EP] European Pat. Off. ............ 94104043.8

[51] Int. Cl.$^6$ ..................................................... A23L 1/105
[52] U.S. Cl. .............................. 426/62; 426/19; 426/20; 426/60; 426/61; 435/254.21; 435/255.2; 435/942
[58] Field of Search .................. 435/254.21, 243, 435/942, 255.2; 426/60, 62, 61, 19, 20

[56] References Cited

U.S. PATENT DOCUMENTS

| | | | |
|---|---|---|---|
| 5,190,877 | 3/1993 | Osinga et al. | 435/256 |
| 5,352,606 | 10/1994 | Takano et al. | 435/255.2 |
| 5,399,492 | 3/1995 | Gysler et al. | 426/62 |
| 5,480,798 | 1/1996 | Gysler et al. | 435/255.2 |

FOREIGN PATENT DOCUMENTS

| | | |
|---|---|---|
| 0 196 233 | 10/1986 | European Pat. Off. |
| 197 497 | 10/1986 | European Pat. Off. |
| 0 306 107 | 3/1989 | European Pat. Off. |
| 0 388 262 | 9/1990 | European Pat. Off. |
| 0 487 878 | 6/1992 | European Pat. Off. |
| 0 556 905 | 8/1993 | European Pat. Off. |
| 61-195637 | 2/1985 | Japan |
| 1-16155 | 3/1989 | Japan |
| 93 01724 | 2/1993 | WIPO |

OTHER PUBLICATIONS

Cold Sensitive Cell–Division–Cycle Matants of Yeast: Isolation, Properties, and Pseudoreversion Studies; D. Moir et al. (Genetics, 100, 547–563, 1982).

Determination of the Order of Gene Function in the Yeast Nuclear Division Pathway Using cs and ts Mutants; D. Moir et al. (Genetics, 100, 565–577, 1982).

Genetic Analysis of Mutations Affecting Growth of Saccharomyces Cerevisiae at Low Temperature; A. Singh et al. (Genetics, 77, 651–659, 1974).

New Freeze–Tolerant Yeast for Dough Preparation; H. Hino et al. (Cereal Chemistry, 64, 269–275, 1987).

Laboratory Technique in Microbological Genetics; Tatsuo Ishikawa Ed., published by Kyoritsu Shuppan K.K. (pp. 180–181), 1982.

Applied Microbiology I; Asakura Shoten K.K., published May 20, 1974 (pp. 199–200).

Saikagaku Jiten, Tokyo Kagaku Dojin K.K., published Apr. 10, 1984 (p. 1288).

*Primary Examiner*—Lien Tran
*Attorney, Agent, or Firm*—Pennie & Edmonds LLP

[57] ABSTRACT

Process for developing a baker's yeast strain having an Lti property, in which a haploid *Saccharomyces cerevisiae* strain having an Lti property is first crossed with a haploid *Saccharomyces cerevisiae* strain having at least one MAL allele which is active but under catabolic repression, then in a second stage, the segregants are crossed, and finally, a prototrophic diploid strain having an Lti phenotype, a Mal phenotype which is active but under catabolic repression, and a potential for growing in a fed-batch process, is selected. Industrial baker's yeast strain *Saccharomyces cerevisiae* which has a growth yield in a fed-batch process of 0.1 to 0.5 g of dry biomass/g of sugar, a $CO_2$ production of less than 15 ml/h/kg of dough up to 8° C., of less than 20 ml/h/kg of dough up to 12° C., and also less than 10 ml per g of compressed yeast up to a temperature of 18° C., after 4 days of culture in maltose-containing medium. The baker's dough including at least water, flour and the above described baker's yeast is disclosed, the dough is preserved at least 2 days under refrigeration.

15 Claims, 3 Drawing Sheets

LOW-TEMPERATURE INACTIVE INDUSTRIAL BAKER'S YEAST AND PROCESS FOR PREPARING SAME

TECHNICAL FIELD

The subject of the present invention is a process for developing industrial strains of baker's yeast having a good Lti property and a good growth yield, industrial baker's yeast strain *Saccharomyces cerevisiae*, in particular those developed according to the present process, and a baker's dough comprising the yeast according to the present invention.

BACKGROUND ART

It is known that the taste and the texture of a baker's dough which is raised with yeasts are quite superior to those of a dough which is raised with chemical agents. Commercial bakery items are also known such as dough for bread rolls and croissants, which are intended to be preserved in a refrigerator before fermentation and baking, and which comprise, nevertheless, a chemical leavening agent.

Accordingly, EP 0,487,878 describes the use of yeast strains having an Lti property, in other words a property of not being very active during refrigeration but of surviving at these temperatures (Lti is the acronym for the expression "low-temperature inactive"), as leavening agent for the production of bread-making items to be baked in an oven after preserving under refrigeration. However, these yeasts are too vigorous, that is to say liberate too much gas at high refrigeration temperatures, that is to say between 8° and 12° C., or even 14° C., which are in fact commonly observed, sometimes during prolonged periods under the usual conditions for the industrial storage of refrigerated products. This vigour can in particular be attributed to the presence, in these strains, of an MAL allele which is active and not repressed by a catabolic pathway, but also to an insufficient selection of the Lti character of these strains. Finally, these yeasts are also not optimized to respond favourably to all the conditions required for their industrial production, such as a good capacity to be dried, or a high growth yield, for example.

Likewise, WO 93/01724 and EP 0,556,905 describe the use of yeast strains having a property similar to that described in EP 0,487,878. However, the strains described belong to a class of Lts mutants (Lts is the acronym for the English expression "low-temperature sensitive"; Singh et al., 1974, Genetics 77, 651–659) which often show a rapid loss of their viability at refrigeration temperatures. Furthermore, these yeasts are poorly adapted to an optimal industrial production and use. Indeed, they are haploid and auxotrophic laboratory yeasts which are hardly capable of being cultivated on traditional industrial media. Furthermore, their growth potential and their productivity on these media are probably low compared with those of an industrial bread-making yeast strain such as the strain "Levure de boulangerie bleue" (LBB) (blue baker's yeast) (Lesaffre, France), for example. Furthermore, the genetic stability of these strains is probably also insufficient to envisage their industrial production. A portion of the production would indeed risk losing the Lts character. Finally, these strains are probably scarcely capable of surviving a traditional drying in the same manner as an industrial baker's strain could survive such a drying.

WO 93/01724 also describes a method for preparing a packaged and refrigerated baker's dough comprising as leavening agent Lts yeasts. In this method, the said dough is prepared by mixing the said yeasts with at least flour and water, this dough is then introduced into a container and sealed, then the dough is raised in the said container which is kept at a refrigeration temperature. A pressurized container is thus obtained containing a refrigerated dough in which the Lts yeasts are supposed to be practically inactive during the entire period in which the container is stored at low temperature.

This method is not however satisfactory for various reasons. Firstly, during the opening of the container, a rapid swelling of the dough is observed due to its decompression. Unfortunately, this swelling is such that it tends to destroy the traditional texture of the dough.

Furthermore, the Lts yeasts are probably capable of liberating too much gas and flavours at high refrigeration temperatures, that is to say between 8° and 12° C. or even 14° C., which are in fact commonly observed under the usual conditions for the industrial storage of refrigerated products. Thus, after a storage time of a few weeks, the internal pressure of the container risks being such that it might be likely to cause it to explode. Furthermore, the concentration of flavours present both in the dough and the container's atmosphere also risks being such that it might be capable of modifying the traditional olfactory and organoleptic qualities of the dough.

In addition, at low refrigeration temperatures, that is to say up to 8° C., the yeasts described are believed not to liberate gas and therefore not to liberate flavours with the consequence of causing the pressure inside the container to rise dramatically. Thus, these flavours are believed to be produced mainly during the raising of the dough, after which few of them are produced. Accordingly, the flavours being unstable by nature, the dough can also rapidly lose its organoleptic qualities during its storage.

Finally, the yeasts were highly activated by the dough raising stage, and it is a problem to envisage inactivating them simply by subjecting the dough containing them to a refrigeration temperature. Indeed, the yeasts then have a highly active fermentative metabolism.

It would consequently be advantageous to promote the appearance of flavours characteristic of a yeast fermentation, during the entire period of preservation of the dough, without however, exceeding a certain concentration. Likewise, it would be advantageous to be able also to remove the limits imposed by the internal pressure of the container.

The object of the present invention is to overcome the disadvantages of the prior art, and thus to provide a process for developing industrial strains of baker's yeast having an Lti property, and a method for preparing a refrigerated baker's dough comprising a strain of yeasts.

SUMMARY OF THE INVENTION

To this end, in the process for developing an industrial strain of baker's yeast having an Lti property, a haploid *Saccharomyces cerevisiae* strain having an Lti property is first crossed with a haploid *Saccharomyces cerevisiae* strain having at least one MAL allele which is active but under catabolic repression, then in a second stage, the segregants are crossed, and finally, a prototrophic diploid strain having an Lti phenotype, a Mal phenotype which is active but under catabolic repression, and a potential for growing in a fed-batch process, is selected.

The industrial baker's yeast strain *Saccharomyces cerevisiae* according to the present invention has a growth yield in a fed-batch process of 0.1 to 0.5 g of dry biomass/g of sugar.

a $CO_2$ production of less than 15 ml/h/kg of dough up to 8° C., of less than 20 ml/h/kg of dough up to 12° C., and also less than 10 ml per g of compressed yeast up to a temperature of 18° C., after 4 days of culture in maltose-containing medium.

The baker's dough according to the present invention comprises at least water, flour and the baker's yeast according to the present invention, and is preserved at least 1 or 2 days under refrigeration.

BRIEF DESCRIPTION OF THE DRAWINGS

FIG. 1:

Representation of the level of $CO_2$ production as a function of time for 100 g of dough comprising 1% compressed yeast, at 8° C., 12° C. and 30° C., for the strains NCIMB 40611, 40612, and a Hindelbank baker's yeast.

FIG. 2:

Three-dimensional representation of the level of $CO_2$ production in a maltose-containing medium as a function of the temperature and the duration for the strain NCIMB 40612.

FIG. 3:

Three-dimensional representation of the level of $CO_2$ production in a maltose-containing medium as a function of the temperature and the duration for the strain "levure de boulangerie bleue" (LB or blue baker's yeast; for comparison).

The expression "MAL allele" is understood to mean in the present disclosure, a complex gene which is part of the MAL gene family encoding three functions, an α-glucosidase, a permease and a regulatary protein. And the expression "MAL allele which is active but under catabolic repression" is understood to mean an MAL allele in which the expression of its functions is repressed by the presence in the culture medium of glucose or sucrose (inducible MAL allele) for example, or an MAL allele which expresses its functions but whose functions themselves are repressed by the presence in the culture medium of glucose or sucrose (constitutive MAL allele), for example.

The term "Lti" is understood in the specification to mean a yeast presenting a low temperature inactivity, that is to say the property of being practically inactive but living in a dough at a temperature of less than or equal to 14° C. of which the dough does not become frozen, and being practically inactive in a maltose-containing medium up to 18° C.

Likewise, the expression "potential for growing" is understood to mean a capacity to be cultivated with a good yield and a good productivity by a process which can be used industrially, especially by the process for the traditional culture of baker's yeast which is known under the name of fed-batch (slow and gradual addition of a sugar solution to a suspension under aeration, so as to avoid the formation of alcohol during the production of biomass and to maximize the yield).

Furthermore, the term "prototrophic" is understood to mean a yeast which develops on a culture medium comprising only a source of carbon, nitrogen, phosphate or sulphur, trace elements and trace amounts of vitamins. This medium may be called "minimum medium".

In addition, the expression "refrigeration temperature" is understood to mean all temperatures of less than or equal to 12° C., even 14° C., at which the dough does not become frozen.

Finally, in the rest of the description, the term "dough" or "baker's dough" designates a traditional baker's dough such as a pizza dough, a bread dough or a croissant dough, for example. These doughs may comprise in particular at least an appropriate quantity of wheat flour, salts, oil and water, for example.

DETAILED DESCRIPTION OF THE INVENTION

Thus, it has been possible to develop remarkable Lti baker's yeast strains having the property of being inactive but living in a dough at refrigeration temperatures, even of still being practically inactive at higher temperatures, that is to say up to 18° C., and restoring the full activity at a fermentation temperature, in particular at a temperature comprised between 25° and 35° C.

These baker's yeast strains also have the property of being more suitable for an industrial use. These strains thus have a growth yield similar, or even equal, to that of a commercial industrial strain, such as the LBB yeast. These strains are also remarkably suitable for drying for the purpose of preserving them without losing their activity in a significant manner after rehydration. Finally, the surprising genetic stability of these yeasts in relation to their Lti character should also be noted.

Finally, a baker's dough prepared by mixing the yeast according to the present invention with at least water and flour becomes saturated with gas after at least 2 days of preservation at a refrigerated temperature, which makes it possible to bake it directly because the presence of gas in the dough is sufficient to make it rise when it is baked. A preliminary stage for raising the dough is thus avoided.

To implement the present process for developing a yeast strain having an Lti property, a haploid *Saccharomyces cerevisiae* strain having an Lti property is first crossed with a haploid *Saccharomyces cerevisiae* strain having at least one MAL allele which is active but under catabolic repression.

To do this, it is possible to choose a haploid *Saccharomyces cerevisiae* strain having a good Lti property, that is to say the capacity to be inactive between 3° and 10° C., for example.

It is also possible to choose a *Saccharomyces cerevisiae* strain having at least one MAL allele under catabolic repression which is inducible, which means that α-glucosidase is not constitutively present in this yeast cultivated in an industrial culture medium. Indeed, these media comprise, as principal sugars, sugars responsible for catabolic repression, for example glucose and/or sucrose. On the other hand, in a baker's dough, this yeast will synthesize α-glucosidase so as to use the dough's maltose only when the sugars responsible for catabolic repression would have been depleted by the yeast. It is thus possible to choose the MAL2, MAL3 or MAL6 allele, for example.

Furthermore, the MAL allele under catabolic repression may also be constitutive, which means that α-glucosidase is present naturally in the yeast while being repressed by the presence of glucose or sucrose in the culture medium. In a baker's dough, this yeast will then directly use the dough's maltose only when the sugars responsible for catabolic repression would have been depleted by the yeast. It is thus possible to choose the MAL2-8c allele, for example.

The diploid progeny derived from the first crossing can then be made to sporulate on a traditional sporulation medium, so as to obtain haploid segregants. At this stage, it is possible to check Mal character of the haploid segregants by cultivating them on a medium comprising, as sole carbon source, maltose, for example the YPM-Agar medium (see section on media). It is also possible to check the Lti character of the haploid segregants by cultivating them on a YPD-Agar medium (see section on media) at a refrigeration temperature of 8°–10 C., for at least 21 days, for example. After at least three weeks, Lti colonies which survive but remain relatively inactive are identified by lack of visible cell growth. This lack of visible cell growth by lti candidates is in sharp contrast to the ample growth of the parental non-Lti haploid strain.

Then, in a second stage, the segregants of opposite sex are crossed with each other on an appropriate medium. It is thus possible to cross segregants obtained from the same first crossing, or to cross segregants obtained from a different first crossing, that is to say a crossing of two segregants each of which have parents which may be different, and of which one of the parents may be the same. A large number of diploid yeast strains having a great diversity of characteristics is thus obtained.

It is possible to check the prototrophic character of the diploid yeasts by cultivating them on minimum medium, for example. The Mal phenotype can also be checked by cultivating them on YPM-Agar medium, for example. The yeasts which have inherited from their parents one or more MAL genes under catabolic repression will thus use maltose and will then be revealed by the pH indicator present in the medium. The diploid character of the yeasts can also be checked by causing them to sporulate on an appropriate medium, for example. Finally, the Lti property of the diploid strains can be checked by cultivating them on YPD-Agar medium at a refrigeration temperature of 8° C. for 21 days, for example. The Lti strains, in this case, develop on it very slowly.

Finally, a prototrophic strain having an Lti phenotype, a Mal phenotype which is active but under catabolic repression, and a potential for growing in a fed-batch process, is selected among these diploid yeast strains as follows.

At this stage, selection criteria which are more strict and more thorough than those used during the preceding stages can therefore be chosen. It is thus possible to select a specific Lti property by subjecting the strains to a test for the production of $CO_2$ in a baker's dough, over several days, at temperatures of between 8° and 14° C., for example.

The said diploid strain can also be selected as a function of a potential for growing in a fed-batch process, by developing it in a culture medium which requires in yeasts a respiratory metabolism of the carbon source(s). The strains having the best exponential growth rate are then selected in a medium which induces a respiratory metabolism of the carbon source(s), preferably the strains having an exponential growth rate equal or greater than 50% of that of a referenced non-Lti industrial baker yeast, such as the LBB strain, for instance equal or greater than 65%, and in particular close to or equal to 100% of that of a referenced non-Lti industrial baker yeast.

By using the development process according to the present invention, it is therefore possible to develop yeast strains which have a remarkable Lti property. Indeed, the repression of the MAL gene causes a delay in activity in the yeasts present in a dough which is subjected to a temperature at which these yeasts become potentially active again. This delay is indeed explained by the fact that the yeasts must first use the sugars responsible for catabolic repression before being able to use maltose, and that these sugars are not present in a quantity sufficient to ensure an optimal fermentative activity of the yeasts.

In addition, this delay is even greater when the Lti yeasts possess an MAL allele which is inducible but under catabolic repression, since indeed the yeast must, in addition, synthesize the functions capable of using maltose after it has used the sugars responsible for catabolic repression. These Lti yeasts are as a result even less sensitive to variations of temperatures above refrigeration temperatures.

These yeasts can therefore be used in the production of bakery items to be baked in an oven after preservation by refrigeration.

It is thus possible to develop industrial bakery strains of *Saccharomyces cerevisiae* which have a growth yield in a fed-batch process of 0.1 to 0.5 g of dry biomass/g of sugar, a $CO_2$ production of less than 15 ml/h/kg of dough up to a temperature of 8° C., of less than 20 ml/h/kg of dough up to 12° C., and a $CO_2$ production of less than 10 ml per g of compressed yeast up to 18° C., after 4 days of culture in maltose-containing medium.

Preferably, the strains have a $CO_2$ production of less than 7 ml/h/kg of dough up to a temperature of 8° C., for instance 0.1 to 7 ml/h/kg, and of less than 12 ml/kg of dough up to 12° C., for instance 0.1 to 12 ml/h/kg.

It is also possible to select yeast strains which have a $CO_2$ production of less than 3 ml/h/kg of dough up to a temperature of 12° C., preferably 0.1 to 3 ml/h/kg.

It is also possible to select yeast strains which have a growth yield in a fed-batch process equal or greater than 0.5 g of dry biomass/g of sugar.

Among various *Saccharomyces cerevisiae* strains thus obtained, two were deposited as examples, in accordance with the Budapest Treaty, on 28.01.94, at the National Collection of Industrial and Marine Bacteria Ltd. (NCIMB), P.O. Box 31, 135 Abbey Road, ABERDEEN AB9 8DG, Scotland (United Kingdom) where they were assigned the numbers NCIMB 40611 and 40612.

The strain NCIMB 40611 has in addition the following characteristics:

Morphology: elliptical cells of relatively homogeneous size.

Fermentation: yeasts capable of fermenting sucrose, glucose and maltose.

Likewise, the strain NCIMB 40612 has the following characteristics:

Morphology: elliptical cells of relatively homogeneous size.

Fermentation: yeasts capable of fermenting sucrose, glucose and maltose.

In a process for preparing a refrigerated and packaged baker's dough, a dough is prepared by mixing a yeast according to the present invention with at least water and flour, then this dough is packaged in a container which comprises a gas outlet valve.

It is thus possible to mix and then package the dough at refrigeration temperatures.

The atmosphere in the container may also be composed of an inert gas such as nitrogen or carbon dioxide, alone or in combination. This atmosphere can be created, for example, by sucking oxygen from the container by vacuum and then injecting the inert gas before sealing the said container. This atmosphere makes it possible in particular to avoid the development of fungi.

In particular, it is also possible to mix the yeast with the dough in an amount of 0.1 to 1% in term of dry matter content of compressed or rehydrated yeast.

These yeasts may, in addition, contain trehalose. And 1.2 to 2% NaCl can be added to the dough in order to reduce the excessive development of the natural dough flora.

The refrigerated dough according to the present invention can be prepared and packaged using the above-described process. This dough has a texture and a flavour which are characteristic of a dough having the same composition and raised by traditional baker's yeasts. It is however possible to prefer the refrigerated dough when the latter is preserved for at least 2 to 60 days at normal refrigeration temperatures. Suprisingly, after 1 or 2 days 2 or 3 of preservation of the dough, the yeasts produce enough gas in the dough to make it rise when it is baked. A preliminary stage for raising the dough is thus avoided.

EXAMPLES

The invention is further described in the following examples which are no way intended to limit the scope of the invention.

The examples below are presented as illustration of the process for developing Lti strains, of a process for preparing a dough, of the Lti strains obtained by the development process, and of the packaged and refrigerated dough obtained by the present preparation process.

The percentages are given by weight unless where otherwise stated. These examples are preceded by a description of various tests, by the composition of various media and by a brief presentation of the drawings.

Tests

1. Production of $CO_2$ in a dough

In order to carry out this test, a baker's dough which will serve as culture medium is prepared. This dough comprises 60.2% flour, 29.2% water, 1.4% NaCl, 7.2% groundnut oil, and 2% Lti yeasts at 15% dry matter. All the ingredients are preserved at 4° C. and the dough is prepared between 4–8° C.

For that, a homogeneous yeast suspension is first prepared by placing a few grams of an Lti yeast suspension at 30% dry matter in a 50 ml Falcon tube, and by adding an equivalent quantity of water so as to obtain a suspension at 15% dry matter, and then stirring the whole. Next, the flour and the salt are mixed, then the groundnut oil and the water are added and finally the Lti yeast suspension is added. Finally, the dough is mixed until it no longer sticks, without however working it excessively. A smooth dough is then obtained. 100 g of this dough are then removed and transferred into a Risograph (RDesign, USA), then the evolution of $CO_2$ is immediately measured.

The evolution of gas is measured first at 8° C. every hour for 120 hours. Then the temperature is increased to 12° C. and the evolution of gas is measured every hour for 120 hours. Finally, the temperature is increased to 30° C. and the evolution of gas is measured every 10 minutes for 6 hours. The activity of the yeasts is then determined by calculating the initial slope for the evolution of gas (ml/g of dough) for each of the temperatures.

2. Growth potential

The aim of this test is to select yeast strains which possess a growth capacity similar to that of industrial yeast strains.

To do this, the yeast strains are cultured in a medium which induces a metabolism similar to that of strains cultured in fed-batch fermentation. It is indeed known that in a traditional fed-batch process, the yeasts assimilate the carbon sources by respiratory metabolic pathways, that they accumulate little or no ethanol or acetate, and that they are capable, in addition, of reassimilating them very rapidly by the respiratory pathways. The strains are thus selected by culturing them on a culture medium which requires the yeasts to perform a respiratory metabolism of the carbon source(s).

For that, the yeasts are cultured in Erlenmeyer flasks (which comprise baffles which promote the aeration of the medium) in a YNEA medium comprising, as carbon source, ethanol and acetate. A small quantity of yeast extract is added with the aim of mimicking the usual industrial media, such as a medium comprising molasses. Furthermore, the medium is buffered to pH 4 with succinate and hydrochloric acid so as to favour the presence of acetate in its acid form.

In this test, the yeasts which are tested are precultured in 5 ml of YPD medium at 30° C., with stirring at about 190 revolutions per minute (rpm) for 12 hours at 30° C. Then, 100 ml of YNE medium (contained in a 500 ml Erlenmeyer flask comprising the baffles) are innoculated with 1 ml of preculture, and incubated for 24 hours at 30° C., with stirring (190 rpm). Finally, 100 ml of YNEA medium (contained in a 500 ml Erlenmeyer flask comprising the baffles) is innoculated with the preceding culture in a quantity such that an OD600 close to 0.1 is reached, and incubated at 30° C., with stirring, for 10 hours, the OD600 being measured every 2 hours.

The strains having the best exponential growth rate are then selected. The strains which have an exponential growth rate at least equal to 65% of that of the LBB strain, in particular close to or equal to 100% of that of the reference LBB strain, are preferably thus chosen.

3. Yield during fed-batch culture

A culture of the selected yeasts is carried out under industrial conditions of fed-batch fermentation. For that, the yeasts are first cultured at 30° C., with stifling, in several containers each containing 400 ml of YPD medium. Then a 30 liter fermenter (Chemap, Switzerland) containing 8 liters of "pre-molasses" medium (see section on "media") is innoculated sterilely with 3 liters of the preceding cultures. Finally, a fermentation is carried out according to the traditional fed-batch process, incubating at 30° C. with stirring (250 to 450 rpm) and increasing aeration (0.02 to 0.8 $m^3/h$), for 24 hours, maintaining the pH at 4.5 by adding adequate quantities of NH4OH, controlling the foam produced by adding increasing quantities of an antifoaming agent such as Contraspum 210 (1.5% weight/volume of medium; Binggeli-Chemie, Switzerland), and adding regularly an adequate increasing quantity of "molasses" medium up to a final volume of about 22 liters.

Finally, the product of this last fermentation is transferred sterilely into a 300 liter fermenter (Chemap, Switzerland) and a fed-batch fermentation is again carried out, incubating at 30° C. with stirring (240 to 350 rpm) and increasing aeration (0.2 to 10 $m^3/h$), for 28 hours, maintaining the pH at 4.5 by adding adequate quantities of NH4OH, controlling the foam produced by adding increasing quantities of an antifoaming agent such as Contraspum (5% weight/volume), and adding regularly an adequate increasing quantity of "molasses" medium for 26 hours up to a final volume of about 180 liters.

During the last two hours of fermentation, no further molasses are therefore added; the quantity of residues of substrate in the medium is thus reduced so as to avoid the presence of sugars which promote the growth of yeasts at a refrigeration temperature.

Finally, the formation of trehalose in the yeasts is thereby also favoured. This storage sugar is relatively important for increasing the viability of the yeasts in a traditional drying process.

The following table 1 illustrates the quantity of "molasses" medium which is added as a function of time, for 30 and 300 liter fermentations.

TABLE 1

| time | 30 liter fed-batch fermentation molasses medium | 300 liter fed-batch fermentation molasses medium |
| --- | --- | --- |
| (h) | (g/h) | (g/h) |
| 1 | 62.5 | 600 |
| 2 | 62.5 | 600 |
| 3 | 62.5 | 700 |
| 4 | 62.5 | 800 |
| 5 | 71 | 900 |
| 6 | 79 | 1000 |
| 7 | 87 | 1100 |
| 8 | 95 | 1200 |
| 9 | 102 | 1300 |
| 10 | 110 | 1400 |
| 11 | 118 | 1500 |
| 12 | 133 | 1600 |
| 13 | 147 | 1700 |
| 14 | 162 | 1800 |
| 15 | 177 | 1900 |
| 16 | 191 | 2000 |
| 17 | 206 | 2100 |
| 18 | 220 | 2200 |
| 19 | 235 | 2300 |
| 20 | 249 | 2400 |
| 21 | 264 | 2500 |
| 22 | 279 | 2600 |
| 23 | 293 | 2700 |
| 24 | 300 | 2800 |
| 25 | /// | 2800 |
| 26 | /// | 2800 |
| 27 | /// | 0 |

The 300 liter fermenter culture is then cooled down to 12° C., then it is centrifuged (Westfalia centrifuge) until about 20% dry matter is obtained, and then the sedimented yeasts are resuspended in water. This suspension is then recentrifuged while washing the biomass during this centifugation with about 300–400 liters of sterile water per 100 liters of suspension.

It is possible to add, at this stage, vitamin C so as to reduce the oxidation of the biomass. Vitamin C also has the advantage of reducing the pH to 4.4.

Finally, the biomass is centrifuged ("De Laval" centrifuge) so as to remove impurities until 28% dry matter is obtained, then the biomass is pressed (Bücher press) until a dry matter of 34 to 35% is obtained. Compressed yeasts are thus obtained.

It is then possible to determine the growth yield of the yeasts. For that, the quantity of dry biomass obtained for the quantity of sugars added during the fermentation (mainly sucrose present in the molasses) is determined.

4. Genetic stability

The genetic stability of a yeast strain for a specific character such as the Lti character is a decisive factor for the industrialization of such a strain.

In order to assess this stability, a search is made for revertants for the Lti character. For that, about $10^8$ cells from a cell culture by an industrial fed-batch process are plated on 10 Petri dishes containing a YPD medium, the dishes are incubated at 8° C., then the colonies which develop at this temperature after about 4 weeks are determined.

5. Production of $CO_2$ under a temperature gradient

This test is carried out in an apparatus specially designed for it, which comprises a temperature gradient unit having chambers at variable temperatures, for example, in which the lower ends of fermentation tubes can be introduced. These tubes have a closed and graduated upper end, as well as an expansion flask branching from the side. The $CO_2$ produced by the yeast accumulates in the graduated upper end of each tube, it being possible for the culture medium displaced by the accumulation of gas to pass into the expansion flask.

To carry out this test, 2 ml of an overnight culture on YPD medium of the strain to be tested are innoculated into 200 ml of a first medium containing 0.67% of an amino acid-free nitrogen base, such as the product marketed by the company Difco under the name "yeast nitrogen base without amino acids", for example, 0.5% yeast extract, 2% sucrose, 1% sodium succinate and concentrated hydrochloric acid to adjust the pH to 4.5, in a 500 ml bottle. The incubation is carried out, with stirring, for 24 h at 30° C.

The cells are separated by centrifugation at 6000 gn at 20° C. for 5 min and they are suspended in 200 ml of a second medium containing 0.67% of an amino acid-free nitrogen base, 0.3% yeast extract and 0.3% sucrose, 1% sodium succinate and concentrated hydrochloric acid in order to adjust the pH to 4.5, in a 500 ml bottle. The incubation is carried out, with stirring, for 24 h at 30° C.

The cells are separated by centrifugation at 6000 gn at 4° C. for 5 min and the pellet of yeast cells which is obtained is washed twice with 50 ml of distilled water.

The cells are suspended in 10 ml of distilled water and they are transferred into graduated and preweighed 15 ml polypropylene tubes. They are centrifuged at 3000 $g_n$ at 4° C. for 10 min. The tubes are drained, the yeast pellets are weighed and they are suspended, in an amount of 0.61 g of yeast pellet equivalent to 0.5 g of compressed yeast having a dry matter content of about 27%, per ml, in a third medium containing 0.67% amino acid-free nitrogen base, 2% maltose, 1% sodium succinate and concentrated hydrochloric acid in order to adjust the pH to 4.5. 0.5 to 3 ml (for temperatures >10° C.) or 1 to 3 ml (for temperatures <10° C.) are introduced into fermentation tubes as described above, each previously filled with 50 ml of the third medium, in other words with the maltose-containing medium, and which was cooled to 4° C.

The fermentation tubes are incubated at the desired temperatures in the temperature gradient unit described above. The production of $CO_2$ is noted at chosen intervals after plunging the tubes for a few seconds in a sonic stirring bath so as to release the $CO_2$ bubbles trapped in the liquid medium.

Media

The percentages of the compounds are given in weight/volume unless where otherwise stated.

YPM-Agar: 1% "Difco Bacto Yeast extract".
    2% "Difco Bacto Peptone".
    2% Maltose.
    2% "Difco Bacto Agar".
    0.9% volume/volume (v/v) of a 0.4% (v/v) solution of Bromcresol Red dissolved in pure ethanol.
YPD: 2% "Difco Bacto Peptone".
    1% "Difco Bacto Yeast extract".
    2% Glucose.
YPD-Agar: YPD containing 2% "Difco Bacto Peptone"
YNE: 0.67% "Difco amino acid-free Yeast Nitrogen Base".
    0.5% "Difco Bacto Yeast extract".
    1% Na2-succinate.
    1.12% (v/v) 5M HCl.
    0.7% (v/v) ethanol.
YNEA: YNE with 0.3% (v/v) of glacial acetic acid.
Premolasses: The initial fed-batch fermentation medium contains the premolasses medium having the following composition:

100 kg of demineralized water
263 g $(NH_4)_2HPO_4$
62 g $MgSO_4$
8.6 g NaCl
7.82 g $CaCl_2$
17 g Inositol
0.84 g Ca-Pantothenate
0.006 g Biotin
Molasses: 84.85% of sterile molasses (Aarberg, Switzerland).
13.85% water
1% $H_2SO_4$.

The sterilization of the molasses is carried out in the following manner. The germination of the contaminating spores is induced by thermal treatment at 80° C. for 30 minutes, allowed to germinate at room temperature for 20 hours, sterilized at 125° C. for 2 minutes, and then after cooling the sediments are separated by centrifugation (Westfalia centrifuge).

Example 1

A haploid *Saccharomyces cerevisiae* strain having an good Lti property, that is to say the capacity to be inactive between 3° and 10° C., such as the strain NCIMB 40613 having the MATα, mal3, Its500 genotype, which was deposited in accordance with the Budapest Treaty on 28.01.94 at the National Collection of Industrial and Marine Bacteria Ltd. (NCIMB), P.O. Box 31, 135 Abbey Road, ABERDEEN AB9 8DG, Scotland (United Kingdom), is used as starting material.

This strain is crossed with a haploid *Saccharomyces cerevisiae* strain comprising an MAL allele which is active but under catabolic repression and inducible, especially the strain NCIMB 40614 having the MATa, trp5, ade7, ade1, MAL6 genotype, deposited on 28.01.94 in accordance with the Budapest Treaty at the same depositing body as that mentioned above.

The diploid yeasts are made to sporulate. Haploid spores are isolated and then their sexual type is characterized by traditional means, their Mal phenotype is checked by culturing them on YPM-Agar medium, and their Lti phenotype is checked by culturing them on YPD-Agar medium at 8° C., for 21 days. After 21 days, Lti colonies which survive but remain relatively inactive are identified by lack of visible growth. This lack of visible cell growth is in sharp contrast to the ample growth of the parental non-Lti haploid strain, that is to say the strain NCIMB 40614.

Approximately 25% of the haploid segregants share the Lti and Mal phenotypes, and then are selected.

Then the selected segregants of opposite sex are crossed with each other, and the diploid prototrophic yeast strains thus obtained are selected as follows.

The Mal phenotype is checked by culturing them on YPM-Agar medium, and the Lti phenotype is characterized by culturing them on YPD-Agar medium at 8° C. as above-described. Approximately 50% of the diploid strains share the Lti and Mal phenotypes, and then are selected.

A Lti property is selected by subjecting the strains to the $CO_2$ production test in a baker's dough as above-described. Approximately 50% of the diploid strains have a $CO_2$ production of less than 15 ml/h/kg of dough up to 8° C., and of less than 20 ml/h/kg of dough up to 12° C. Approximately 60% of the diploid strains have a $CO_2$ production of less than 7 ml/h/kg of dough up to 8° C., and of less than 12 ml/h/kg of dough up to 12° C.

A grow potential in a fed-batch process is selected by culturing them according to the preceding "growth potential" test. Approximately 50% of the diploid strains have an exponential growth rate greater than 65% of that of the referenced LBB strain. Approximately 30% of the diploid strains have an exponential growth rate greater than 80% of that of the referenced LBB strain. Approximately 12% of the diploid strains have an exponential growth rate greater than 90% of that of the referenced LBB strain Among the various strains thus obtained, the strain LCG2 was deposited as example, and received the deposit number NCIMB 40611 as mentioned above.

Figure 1:
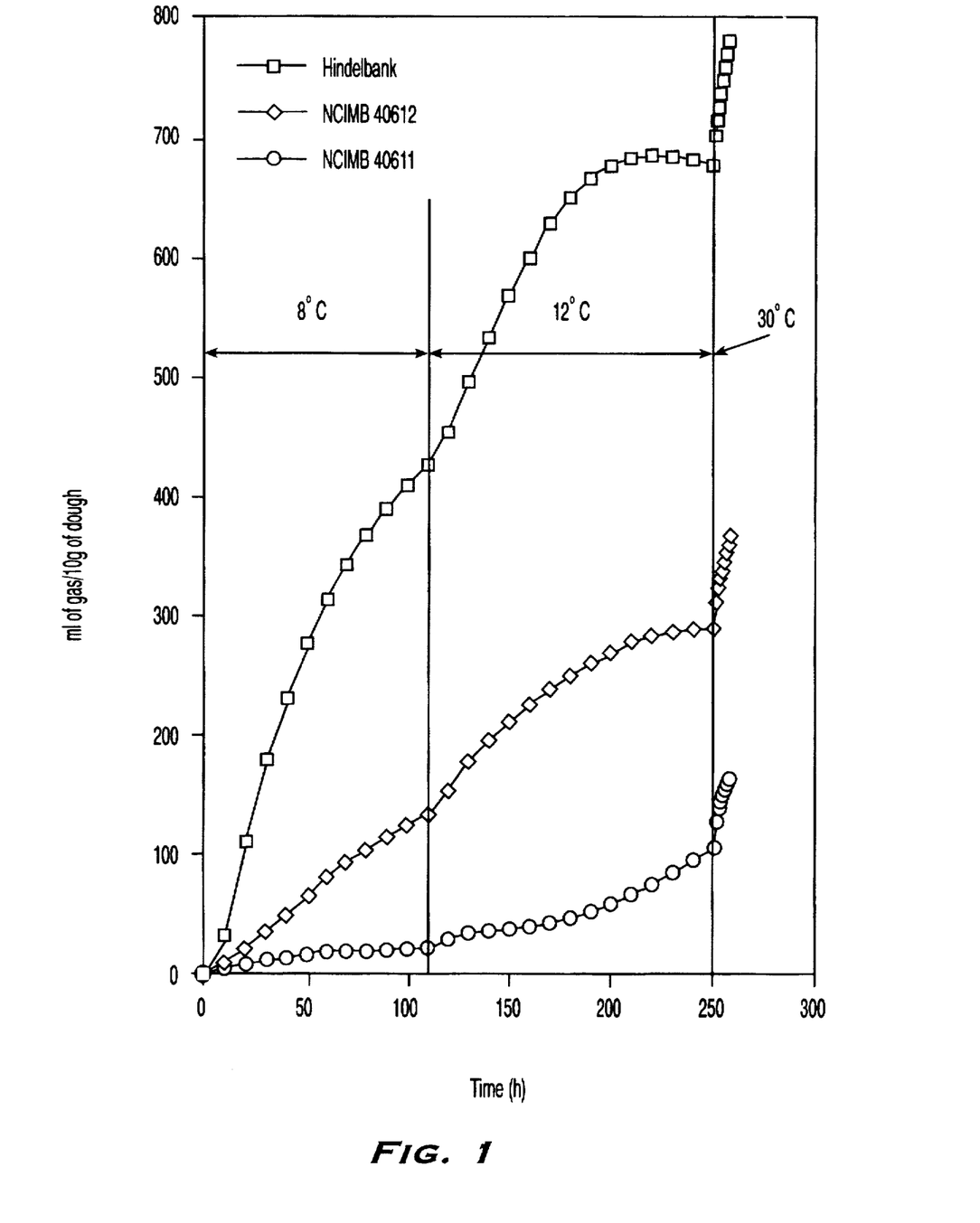

This strain has a remarkable Lti property. As can be seen in FIG. 1 which illustrates the results obtained according to the "production of $CO_2$ in a dough" test, this strain is practically inactive between 3 and 12° C. It has, indeed, a $CO_2$ production of less than 3 ml/h/kg of dough at a temperature of 3–12° C. It is also observed that the level of $CO_2$ production at 30° C. rises rapidly.

Furthermore, the results obtained by the "production of $CO_2$ under a temperature gradient" test shows that this strain does not release any gas up to 18° C., after 12 days of culture in maltose-containing medium.

In addition, this strain has an exponential growth rate equal to 66% of that of the LBB yeast, and a growth yield in a fed-batch process, according to the test described earlier, which is equivalent to that which is determined in the same manner for the LBB strain, that is to say 0.5 g of dry biomass/g of sugar.

Finally, no revertants are found according to the test of genetic stability described above. This strain is thus particularly stable.

Example 2

A haploid *Saccharomyces cerevisiae* strain having an Lti property, such as the strain NCIMB 40613 having the MATE, mal3, Its500 genotype, which was deposited in accordance with the Budapest Treaty on 28.01.94 at the National Collection of Industrial and Marine Bacteria Ltd. NCIMB), P.O. Box 31, 135 Abbey Road, ABERDEEN AB9 8DG, Scotland (United Kingdom), is used as starting material.

This strain is crossed with a haploid *Saccharomyces cerevisiae* strain comprising an MAL allele which is active but under catabolic repression and constitutive, 30 especially the strain NCIMB 40615 having the MATa, leu2, trpl, ura3, MAL2-8c, MAL3 genotype, deposited in accordance with the Budapest Treaty on 28.01.94.

The diploids are made to sporulate, then the segregants are crossed and strains are selected in the same manner as in Example 1. The screening numerical ranges are also similar to those of the Example 1.

Among various strains thus obtained, the strain LCG22 was deposited as example, and received the deposit number NCIMB 40612 as mentioned above.

As can be seen in FIG. 1 which illustrates the results obtained according to the "production of $CO_2$ in a dough" test, this strain is practically inactive between 3 and 12° C. It has, indeed, a $CO_2$ production of less than 7 ml/h/kg of dough at a temperature of 3-8° C. and of less than 12 ml/h/kg of dough at at least 12° C., and it is also observed that the level of $CO_2$ production at 30° C. rises rapidly.

Figure 2:
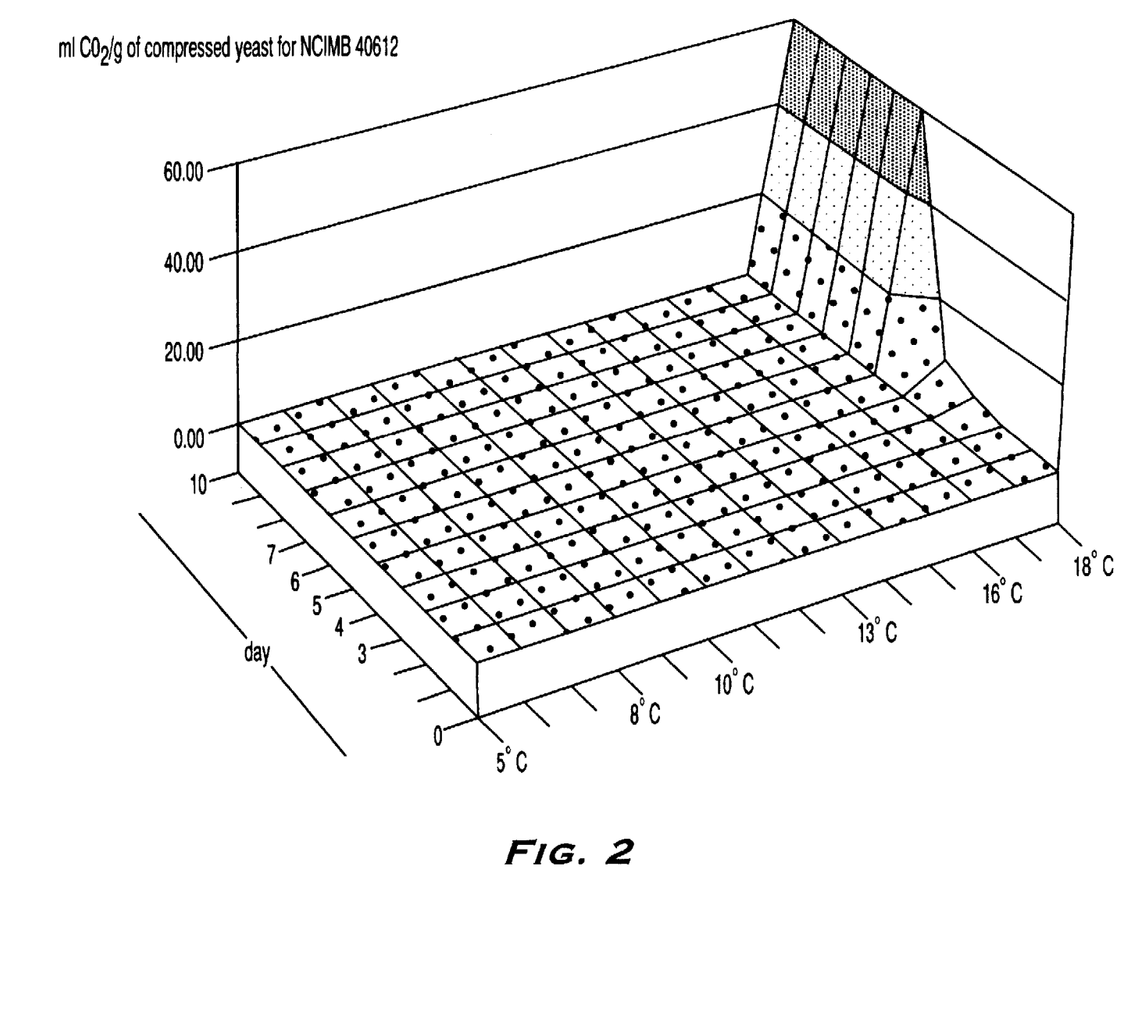
Figure 3:
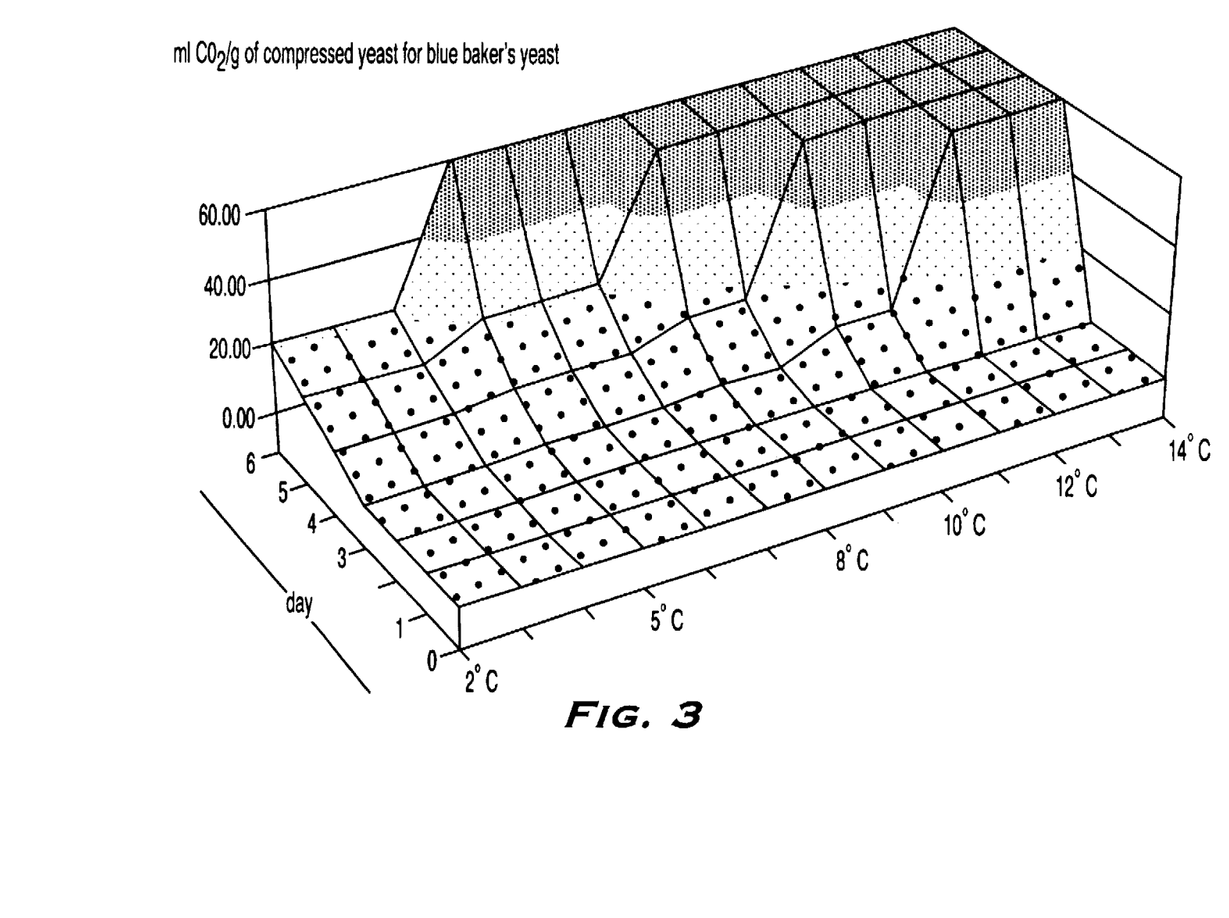

Furthermore, as can be seen in FIG. 2 which illustrates the results obtained by the "production of $CO_2$ under a temperature gradient" test, this strain has, in addition, a $CO_2$ production of less than 10 ml per g of compressed yeast up to 18° C., after 4 days of culture in maltose-containing medium. For comparison, this test was also carried out for the reference LBB strain (see FIG. 3).

In addition, this strain has an exponential growth rate equal to 90% of that of the LBB yeast, and a growth yield in a fed-batch process, according to the test described earlier, which is equivalent to that which is determined in the same manner for the LBB strain, that is to say 0.5 g of dry biomass/g of medium.

Finally, no revertants are found according to the test of genetic stability described above. This strain is thus also particularly stable.

Example 3

The Lti baker's yeasts are dried so as to be able to preserve them for a long period in the form of a powder, in the following manner. A culture of the strain NCIMB 40612, centrifuged and washed, comprising about 20% dry matter, is used. The yeast is then dried in a traditional manner, for example as described in U.S. Pat. No. 4,358,250. A dry yeast powder comprising 96% dry matter is thus obtained.

These yeasts are then rehydrated in the following manner. 10% dry yeast is added to 90% water at 30C, and then mixed gently for 20 minutes, and finally, a quantity of water is added at 4° C. so as to obtain a yeast suspension having a desired dry matter content.

It can be noted that the dehydrated and then rehydrated yeast fully preserves its fermentative activity.

Example 4

A refrigerated and packaged baker's dough comprising the compressed yeast strain NCIMB 40612 is prepared. For that, a compressed fresh culture of NCIMB 40612 yeast is used as described earlier in the "fed-batch culture yield" test.

A quantity of these compressed yeasts (comprising about 35% dry matter) is then mixed with flour, water, fat and salt so as to have a dough comprising 0.2% compressed yeast dry matter, 60% flour, 30% water, 8% margarine and 1.8% NaCl.

This dough is then packaged in the same manner as that described in Patent EP 0,158,590, with the difference that the plastic packaging, which is impervious to air, comprises a gas outlet valve, that is to say a valve which permits the outflow of gas from the inside of the packaging to the outside and which prevents the inflow of air from the outside to the inside of the packaging. Furthermore, the internal atmosphere of this packaging also comprises 50% nitrogen and 50% carbon dioxide.

Example 5

A refrigerated and packaged baker's dough comprising the compressed yeast strain NCIMB 40611 is prepared. For that, a compressed fresh culture of NCIMB 40611 yeast is prepared as described earlier in the "fed-batch culture yield" test. A quantity of the compressed culture is then mixed with flour, water, fat and salt in a ratio identical to that of the example 4, and the dough is then packaged in the same manner as that described in the example 4.

Example 6

A refrigerated and packaged baker's dough comprising the rehydrated yeast strain NCIMB 40612 is prepared. The rehydrated NCIMB 40612 yeast suspension of Example 3 comprising 10% dry matter is used, and a dough comprising 0.3% rehydrated yeast dry matter, 60% flour, 30% water, 8% margarine and 1.7% NaCl is thus prepared. Then the dough is packaged in the same manner as in Example 4.

Example 7

The dough of Example 4 which has been preserved at a refrigeration temperature for 1 day is used, then the dough is directly baked at 220° C., for about 15 minutes.

Likewise, the doughs of Example 4 preserved by refrigeration for 2, 7, 28 and 60 days respectively were baked in the same manner as above.

Finally, for comparison, a dough is prepared having the same composition as that described in Example 4, the only difference being that LBB (Hirondelle, Lesaffre S.A., France) baker's yeasts are added in place of the Lti yeasts. The dough is raised for 45 minutes at room temperature, then the dough is baked under the same conditions as those described above.

The three baked doughs which were preserved for 2, 7, 28 and 60 days have a taste and a texture which are very similar to those of a dough which was raised with yeasts in the traditional manner above.

On the other hand, the baked dough which was preserved for 1 day has a taste and a texture which are a little different from those of a dough which was raised by yeasts in a traditional manner. This can be explained by the fact that during the first day of preservation, the NCIMB 40612 yeasts have not yet produced enough flavour and gas for the dough to be very similar to a traditional dough.

Example 8

The dough of Example 5 which has been preserved at a refrigeration temperature for 2, 3, 7, 28 and 60 days respectively were baked in the same manner as that of the example 7.

The four baked doughs which were preserved for 3, 7, 28 and 60 days have a taste and a texture which are very similar to those of the traditional dough of the example 7 which was raised with LBB yeasts.

On the other hand, the baked dough which was preserved for 2 days has a taste and a texture which are a little different from those of a dough which was raised by LBB yeasts. This can be explained by the fact that during the two first days of preservation, the NCIMB 40611 yeasts have not yet produced enough flavour and gas for the dough to be very similar to a traditional dough.

The present invention is not to be limited in scope by the specific embodiments described herein. Indeed, various modifications of the invention in addition to those described herein will become apparent to those skilled in the art from the forgoing description and accompanying figures. Such modifications are intended to fall within the scope of the claims. Various publications are cited herein, the disclosures of which are incorporated by reference in their entireties to the extent necessary to understand the present invention.

We claim:

1. A process for developing a baker's yeast which comprises crossing a haploid *Saccharomyces cerevisiae* strain which is inactive between about 3 and 10° C. with a haploid *Saccharomyces cerevisiae* strain having at least one MAL allele which is active but under catabolic repression to form a first diploid strain; sporulating the first diploid strain to obtain haploid segregants; culturing the haploid segregants to identify those which have the MAL allele and which are substantially inactive at a temperature of between about 3° and 18° C.; crossing the identified haploid segregants to form second diploid strains; and selecting a prototrophic diploid strain having an Lti phenotype characterized as being inactive but living in a dough at a temperature of less than or equal to about 14° C. of which the dough does not become frozen and being substantially inactive in a maltose containing medium up to a temperature of 18° C., a Mal phenotype which is active but under catabolic repression, and a potential for growing in a fed-batch process as the baker's yeast.

2. The process according to claim 1, wherein the haploid segregants are derived from different first crossings, are crossed to obtain the prototrophic diploid strain.

3. The process according to claim 1, wherein the MAL allele is constitutive or inducible in the yeast.

4. The process according to claim 1, wherein the Lti property of the prototrophic diploid strain is checked by subjecting the strain to a test of production of $CO_2$ in a baker's dough, for several days, at temperatures of between about 3° and 30° C.

5. The process according to claim 1, wherein the growth potential in a fed-batch process of the prototrophic diploid strain is checked by developing the strain in a culture medium which requires a respiratory metabolism of the carbon source(s).

6. An industrial baker's yeast strain *Saccharomyces cerevisiae* which has a growth yield in a fed-batch process of 0.1 to 0.5 g of dry biomass/g of sugar, a $CO_2$ production of less than 15 ml/h/kg of dough at temperatures of up to 8° C., a $CO_2$ production or less than about 20 ml/h/kg of dough at temperatures of up to 12° C., and a $CO_2$ production of less than 10 ml per g of compressed yeast at temperatures of up to 18° C., after 4 days of culture in maltose-containing medium.

7. The yeast strain according to claim 6 which has an exponential growth rate in a medium requiring in yeasts a respiratory metabolism of the carbon source(s), equal or greater than 50% of that of a non-Lti industrial baker yeast.

8. The yeast strain according to claim 6 which has a growth yield in a fed-batch process greater than 0.5 g of dry biomass/g of sugar.

9. The yeast strain according to claim 6, characterized in that it has a $CO_2$ production of less than 3 ml/h/kg at temperatures of up to 12° C.

10. Industrial baker's yeast strain chosen from the group consisting of the *Saccharomyces cerevisiae* strains NCIMB 40612 and NCIMB 40611.

11. A dough comprising at least water, flour and the baker's yeast according to claim 6.

12. The dough according to claim 11 which is preserved for at least 2 to 3 days under refrigeration.

13. The yeast strain according to claim 6 wherein the $CO_2$ production is less than 7 ml/h/kg of dough at temperatures of up to 8° C. and the $CO_2$ production is less than 12 ml/h/kg of dough at temperatures of up to 12° C.

14. A dough comprising at least water, flour and the baker's yeast according to claim 13.

15. The dough according to claim 14 which is preserved for at least 2 to 3 days under refrigeration.

* * * * *